(12) United States Patent
Laird, Jr. et al.

(10) Patent No.: US 10,820,896 B2
(45) Date of Patent: Nov. 3, 2020

(54) SURGICAL RETRACTOR

(71) Applicant: GLOBUS MEDICAL, INC., Audubon, PA (US)

(72) Inventors: David Laird, Jr., Brandamore, PA (US); Andrew Davison, Downingtown, PA (US); Gabrielle Zingalis, Philadelphia, PA (US); Michelle Gray, Oley, PA (US)

(73) Assignee: Globus Medical Inc., Audubon, PA (US)

( * ) Notice: Subject to any disclaimer, the term of this patent is extended or adjusted under 35 U.S.C. 154(b) by 127 days.

(21) Appl. No.: 16/002,258

(22) Filed: Jun. 7, 2018

(65) Prior Publication Data

US 2018/0353164 A1   Dec. 13, 2018

Related U.S. Application Data

(60) Provisional application No. 62/518,022, filed on Jun. 12, 2017.

(51) Int. Cl.
    *A61B 17/02*    (2006.01)
    *A61B 1/32*    (2006.01)
    (Continued)

(52) U.S. Cl.
CPC ............ *A61B 17/0218* (2013.01); *A61B 1/32* (2013.01); *A61B 17/0206* (2013.01); *A61B 17/2812* (2013.01); *A61B 2017/0092* (2013.01); *A61B 2017/00407* (2013.01); *A61B 2017/00442* (2013.01); *A61B 2017/00473* (2013.01); *A61B 2017/00477* (2013.01);
(Continued)

(58) Field of Classification Search
CPC ............ A61B 1/32; A61B 2017/00442; A61B 2017/00946; A61B 17/02; A61B 17/0206; A61B 17/0218; A61B 2017/0225; A61B 17/0293; A61B 17/28; A61B 17/2812; A61B 2017/2837; A61B 17/29
See application file for complete search history.

(56) References Cited

U.S. PATENT DOCUMENTS 1,506,032 A    8/1924    Stevens
5,728,047 A * 3/1998    Edoga .................... A61B 17/02
                                                                    600/102
(Continued)

FOREIGN PATENT DOCUMENTS

DE        8607483        7/1986
JP      2007514501 A    6/2007
(Continued)

*Primary Examiner* — Larry E Waggle, Jr.

(57) ABSTRACT

A surgical retractor is disclosed herein. In some embodiments, a surgical retractor includes a body extending from a proximal end to a distal end and having a first portion coupled to a second portion via a hinged connection, wherein the first and second portions are configured to rotate about a body axis; a first radiolucent tip coupled to a distal portion of the first portion; a second radiolucent tip coupled to a distal portion of the second portion; a holder coupled to one of the first or second portions; and a deformable member extending through the holder, wherein the deformable member is configured to be deformed to facilitate fixation of the surgical retractor at a desired location.

20 Claims, 3 Drawing Sheets

(51) Int. Cl.
*A61B 17/28* (2006.01)
*A61B 17/00* (2006.01)

(52) U.S. Cl.
CPC ........... *A61B 2017/00915* (2013.01); *A61B 2017/00946* (2013.01); *A61B 2017/0225* (2013.01); *A61B 2017/2837* (2013.01)

(56) References Cited

U.S. PATENT DOCUMENTS

| | | |
|---|---|---|
| 6,887,198 B2 | 5/2005 | Phillips et al. |
| 7,389,710 B2 * | 6/2008 | Phillips .................. A61B 17/02 |
| | | 74/577 M |
| 8,876,904 B2 * | 11/2014 | Pimenta ............... A61B 5/0488 |
| | | 623/17.16 |
| 2004/0158286 A1 | 8/2004 | Roux et al. |
| 2007/0299315 A1 | 12/2007 | Geller |
| 2012/0245431 A1 | 9/2012 | Baudouin et al. |
| 2012/0296172 A1 * | 11/2012 | Raven, III ......... A61B 17/0206 |
| | | 600/231 |
| 2014/0243606 A1 | 8/2014 | Santilli |

FOREIGN PATENT DOCUMENTS

| | | |
|---|---|---|
| JP | 2010069321 A | 4/2010 |
| JP | 2015037564 A | 2/2015 |
| WO | 2013148678 | 10/2013 |

\* cited by examiner

SURGICAL RETRACTOR

CROSS-REFERENCE TO RELATED APPLICATIONS

The present application claims the benefit of U.S. Provisional Patent Application No. 62/518,022, filed Jun. 12, 2017, which is hereby incorporated by reference in its entirety for all purposes.

FIELD OF THE INVENTION

The invention generally relates to devices and methods that improve surgical procedures by, for example, providing a working space for the procedure and improving the surgical conditions for the practitioner of a procedure.

BACKGROUND OF THE INVENTION

In surgical procedures generally, surgeons try to keep incisions as small as possible to minimize or reduce trauma to the patient and damage to tissue. However, it is usually necessary that the surgeon have a clear view of the operating field. Also, an opening may need to be enlarged to accommodate the passing of medical implants therethrough.

A variety of retractors, such as, for example, weitlaners, are available for use in surgical operations to reposition muscular tissue, vessels, nerves, and other tissue with the aid of retractor blades, thereby providing access to the site of the operation. However, many current retractors have several shortcomings. For example, weitlaners are prone to falling out of the incision during a procedure. In some cases, the retractors would fall on the floor or another non-sterile area, rendering them useless. Also, weitlaners are not radiolucent and, therefore, require removal from the incision before radiographic images (e.g., x-rays) of the area beneath them are taken; otherwise they will appear in the images and impede visualization the area beneath them (e.g., a fracture beneath the weitlaners).

Therefore, a need exists for a retractor system that overcomes or minimizes these and other problems.

SUMMARY

Embodiments of surgical retractors are disclosed herein. In some embodiments, a surgical retractor includes a body extending from a proximal end to a distal end and having a first portion coupled to a second portion via a hinged connection, wherein the first and second portions are configured to rotate about a body axis; a first radiolucent tip coupled to a distal portion of the first portion; a second radiolucent tip coupled to a distal portion of the second portion; a holder coupled to one of the first or second portions; and a deformable member extending through the holder, wherein the deformable member is configured to be deformed to facilitate fixation of the surgical retractor at a desired location.

In some embodiments, a handheld surgical retractor includes a body extending from a proximal end to a distal end and having a first portion coupled to a second portion via a hinged connection, wherein the first and second portions are configured to rotate about a body axis, and wherein a distal portion the first portion of the body includes a first hole and a distal portion of the second portion of the body includes a second hole; a first radiolucent tip coupled to the distal portion of the first portion and having a third hole corresponding to the first hole; a second radiolucent tip coupled to the distal portion of the second portion and having a fourth hole corresponding to the second hole; a first pin extending through the first and third holes to couple the first radiolucent tip to the first portion of the body; a second pin extending through the second and fourth holes to couple the second radiolucent tip to the second portion of the body; a holder coupled to one of the first or second portions; and a deformable member extending through the holder, wherein the deformable member is configured to be deformed to facilitate fixation of the surgical retractor at a desired location.

In some embodiments, a surgical retractor includes a body extending from a proximal end to a distal end and having a first portion coupled to a second portion via a hinged connection, wherein the first and second portions are configured to rotate about a body axis; a holder coupled to one of the first or second portions; a first radiolucent tip coupled to a distal portion of the first portion; and a second radiolucent tip coupled to a distal portion of the second portion.

BRIEF DESCRIPTION OF THE DRAWINGS

The invention will be more readily understood with reference to the embodiments thereof illustrated in the attached figures, in which.

DETAILED DESCRIPTION

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

The terms "first position," "second position," and "third position," as used herein, merely refer to dissimilar positions and are not meant to imply that all embodiments can only be adjusted to one, two, or three positions. In some embodiments, a surgical retractor may be adjustable to a finite number of positions. In other embodiments, the distance between one or more components can be increased or decreased to any desired extent, thereby allowing a surgical retractor to adjust to an almost infinite number of positions.

Figure 1:
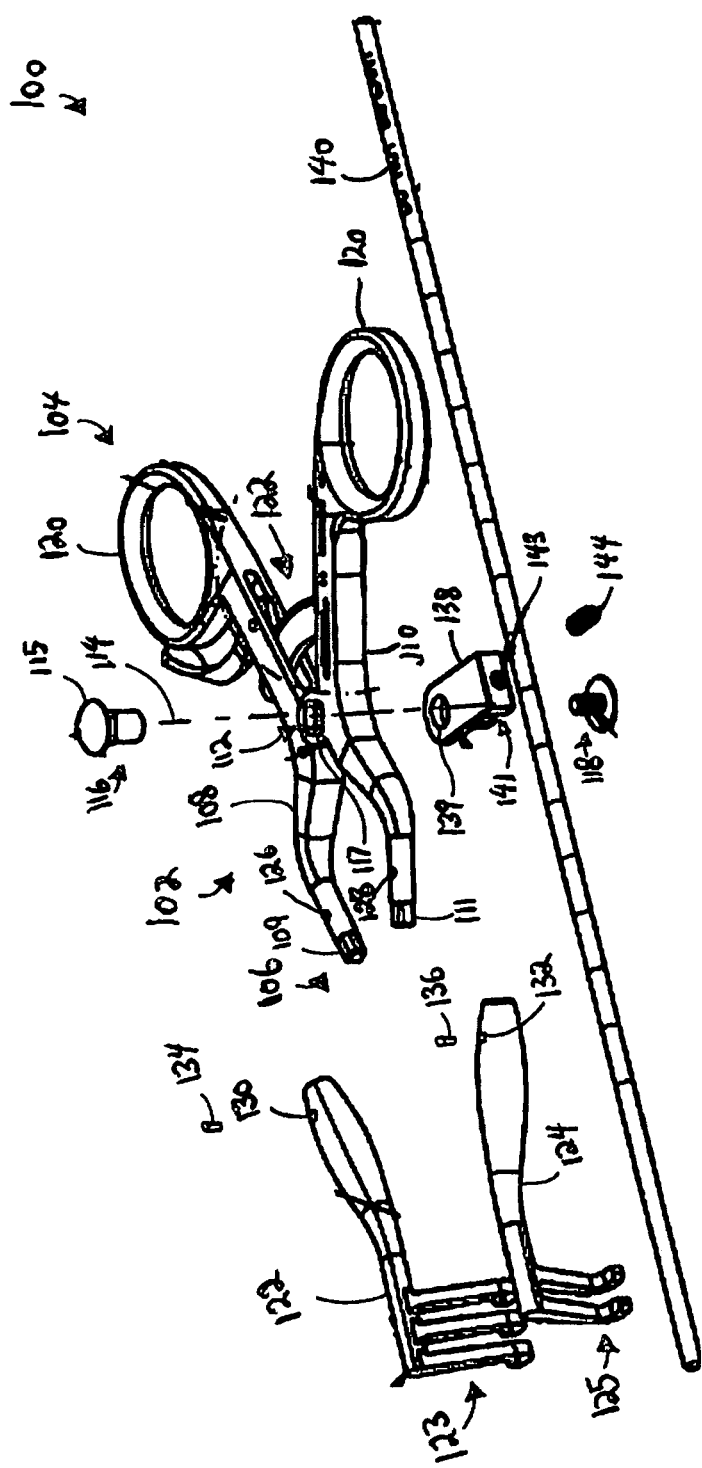
FIG. 1 is an exploded isometric view of a surgical retractor in accordance with embodiments of the present invention.
Figure 2A:
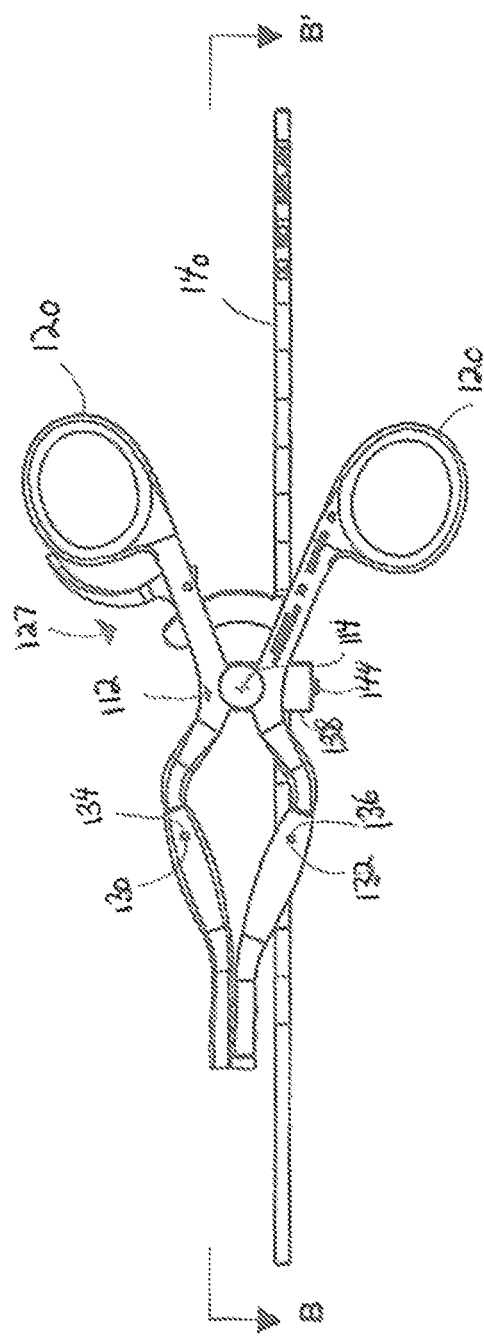
FIG. 2A is a top view of a surgical retractor in accordance with embodiments of the present invention.
Figure 2B:
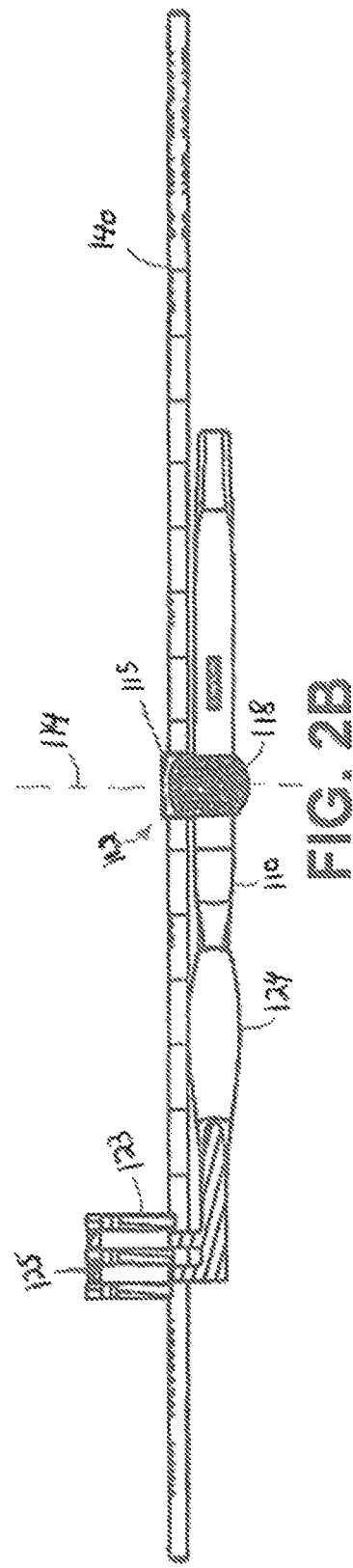
FIG. 2B is a cross-sectional view of the surgical retractor of FIG. 2A taken along line B-B'.

The following description is made with reference to FIGS. 1-2B. FIG. 1 depicts an isometric exploded view of a surgical retractor 100 (e.g., a handheld surgical retractor) in accordance with embodiments of the present invention. FIGS. 2A and 2B depict top and cross-sectional views, respectively, of the surgical retractor 100. In some embodiments, the surgical retractor 100 may be a handheld surgical retractor such as, for example, a pair of weitlaners. The surgical retractor 100 includes a body 102 extending from a proximal end 104 to a distal end 106. In some embodiments, the body 102 may be formed of any material suitable for use at a surgical site such as, for example, stainless steel. The body 102 includes a first portion 108 coupled to a second portion 110 via a hinged connection 112 such that the first and second portions 108, 110 are rotate about a body axis 114. As shown more clearly in FIGS. 1 and 2B, the hinged connection 112 may include a sleeve 116 extending through an opening 117 formed through the body 102 (i.e., through the first and second portion 108, 110) and having an opening to receive a fixation element 118. The sleeve 116 includes an enlarged head 115 which abuts the body 102 when a portion of the sleeve 116 extends through the opening 117. In some embodiments, the sleeve 116 may include internal threads and the fixation element 118 may be a screw having external threads corresponding to the internal threads of the sleeve 116. In some embodiments, the fixation element 118 may alternatively be bonded to the sleeve 116 via any conventional manner such as, for example, welding, adhesives, etc. Each of the first and second portions 108, 110 include a finger ring 120 at the proximal end 104 to facilitate use of the surgical retractor 100 with a user's fingers.

Figure 3:
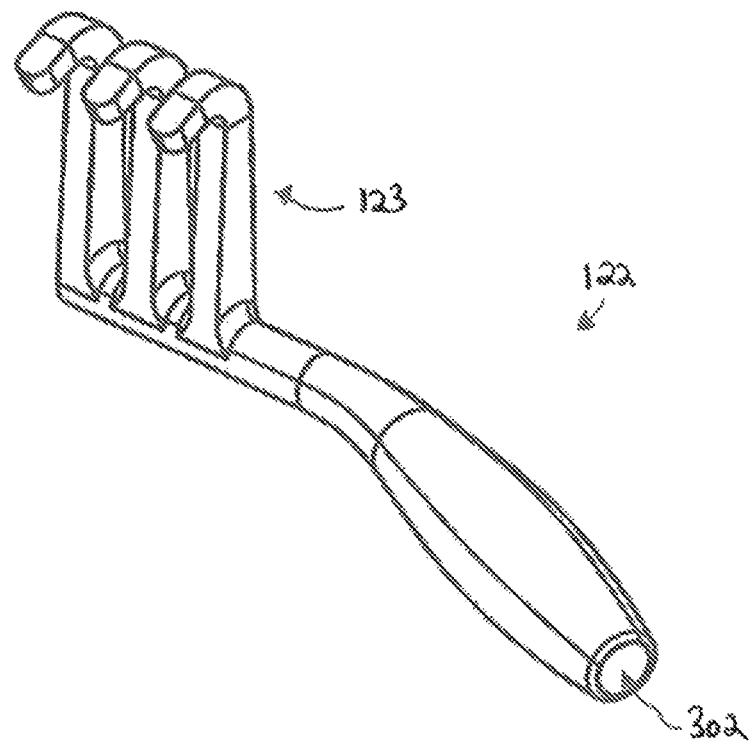
FIG. 3 is an isometric view of a radiolucent tip of a surgical retractor in accordance with embodiments of the present invention.

First and second tips 122, 124 are coupled to the distal end 106 of the body 102 (i.e., to a distal portion 109 of the first portion 108 and a distal portion 111 of the second portion 110, respectively). FIG. 3 depicts an isometric view of the first tip 122 in accordance with some embodiments of the present invention. It should be noted, however, that FIG. 3 may alternatively be a depiction of the second tip 124. To couple the first tip 122 to the first portion 108, a distal end of the first portion 108 is inserted into an opening 302 formed in the first tip 122. In some embodiments, the diameter of the distal end of the first portion 108 may be larger than the diameter of the opening 302 such that the distal end of the first portion 108 is press fit into the first tip 122. In some embodiments, the distal end of the first portion 108 may alternatively be coupled to the first tip 122 via other means, as discussed below. Although this description has been made with regard to the first tip 122, it should be noted that the second tip 124 is configured similar to the first tip 122. As such, this description also applies to the second tip 124.

As noted above, the inventors have discovered that conventional retractor tips obscure a surgical site (e.g., an incision in which the retractor is used) to be viewed in radiographic images such as, for example, X-rays. As such, the first and second tips 122, 124 may be formed of a radiolucent material (herein after first radiolucent tip 122 and second radiolucent tip 124) such as, for example, aluminum, to advantageously allow for radiographic images of the surgical site to be taken without removing the surgical retractor 100 from the surgical site. The first radiolucent tip 122 includes a first plurality of tines 123 extending from a distal portion of the first radiolucent tip 122. Similarly, the second radiolucent tip 124 includes a second plurality of tines 125 extending from a distal portion of the second radiolucent tip 124. When the surgical retractor 100 is in a first position (shown in FIG. 2A), the second plurality of tines 125 extend between corresponding ones of the first plurality of tines 123. When the surgical retractor 100 is in a second position (shown in FIG. 1), the first and second plurality of tines 123, 125 are spaced apart from one another to engage a features of a surgical site to space the features apart (e.g., in a surgical incision to widen the opening). In some embodiments, one of the first and second pluralities of tines 123, 125 may include one more tine than the other one of the first and second pluralities of tines 123, 125 (as shown in FIG. 1).

In some embodiments, the distal portion 109 the first portion 108 may include a first hole 126 and the distal portion 111 of the second portion 110 may include a second hole 128. Similarly, the first radiolucent tip 122 may include a third hole 130 corresponding to the first hole 126 and the second radiolucent tip 124 may include a fourth hole 132 corresponding to the second hole 128. In such an embodiment, the surgical retractor 100 further includes a first pin 134 configured to be pressed into the first and third holes 126, 130 to couple the first radiolucent tip 122 to the first portion 108 of the body 102 and a second pin 136 configured to be pressed into the second and fourth holes 128, 132 to couple the second radiolucent tip 124 to the second portion 110 of the body 102. Such a configuration advantageously allows for easy removal and cleaning of the first and second radiolucent tips 122, 124. However, it should be noted that the first and second radiolucent tips 122, 124 may be coupled to the first and second portions 108, 110 in any alternative suitable manner. For example, the distal ends of the first and second portions 108, 110 may alternatively include a feature that is press fit into the first and second radiolucent tips 122, 124 to removably couple the tips to the body 102. Alternatively, the radiolucent tips may alternatively be permanently coupled to the body via, for example, welding or adhesives.

Figure 4:
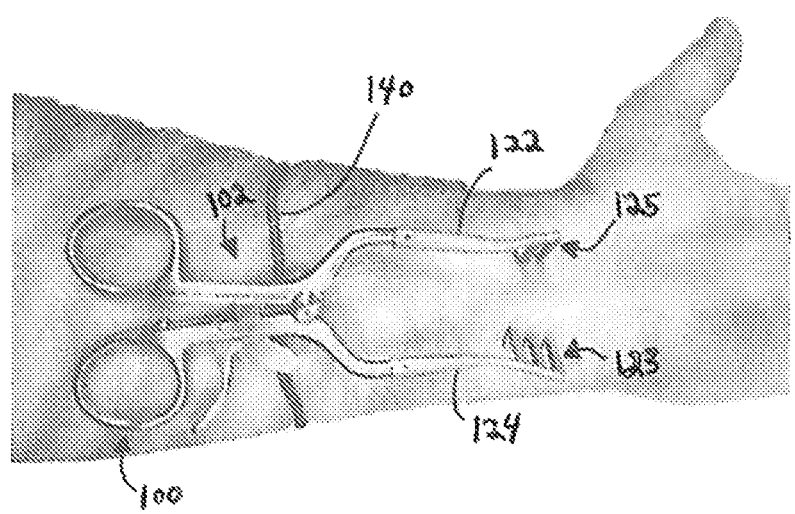
FIG. 4 illustrates a surgical retractor deployed at a surgical site in accordance with embodiments of the present invention.

As previously noted, conventional retractors can fall out of surgical sites onto non-sterile surfaces such as the floor, rendering the retractors useless until properly cleaned. To address this drawback, the inventive surgical retractor 100 includes a holder 138 coupled to one of the first or second portions 108, 110 and a deformable member 140 (e.g., a deformable rod) extending through the holder 138. The deformable member 140 is configured to be deformed to facilitate fixation of the surgical retractor 100 at a desired location. For example, if the user is performing a procedure on a patient's wrist, the deformable member 140 may be deformed such that the rod curls around the patient's wrist, as illustrated in FIG. 4, to hold the surgical retractor 100 in place and prevent it from falling off. In some embodiments, the holder 138 is rotatably coupled to the body 102 such that the holder 138 (and the deformable member 140) is free to rotate about the body axis 114 when the holder 138 is coupled to the body 102; thus advantageously providing the user with more flexibility as to how the deformable member 140 can be deployed at a surgical site.

As shown more clearly in FIG. 1, in some embodiments, the holder 138 may include a through hole 139 through which the sleeve 116 may extend after it extends through the opening 117. The diameter of the through hole 139 is slightly larger than the outer diameter of the sleeve 116 such that the holder 138 is allowed to rotate about the body axis 114 when the holder 138 is coupled to the body 102. The holder 138 further includes a channel 141 configured to receive the deformable member 140. In some embodiments, the holder 138 may further include a threaded hole 143 extending perpendicularly to the channel 141 and a set screw 144 configured to be threaded into the threaded hole 143 to exert a force perpendicular to the deformable member 140 when disposed within the channel 141. As a result, the deformable member 140 is securely held within the channel 141.

In some embodiments, a portion of the body 102 of the surgical retractor 100 includes a ratchet pawl assembly 127 disposed proximate of the holder 138 and configured to prevent movement of the surgical retractor 100 towards the first position once the surgical retractor 100 has been forced into the second position (i.e., by forcing the two finger rings 120 towards each other).

While the invention herein disclosed has been described with reference to specific embodiments and applications thereof, numerous modifications and variations can be made thereto by those skilled in the art without departing from the scope of the invention as set forth in the claims.

What is claimed is:

1. A surgical retractor; comprising:
   a body extending from a proximal end to a distal end and having a first portion coupled to a second portion via a hinged connection, wherein the first and second portions are configured to rotate about a body axis;
   a first radiolucent tip coupled to a distal portion of the first portion;
   a second radiolucent tip coupled to a distal portion of the second portion;
   a holder coupled to one of the first or second portions; and
   a deformable member extending through the holder and having a first free end and a second free end opposite the first free end, wherein the deformable member is configured to be deformed around human tissue to facilitate fixation of the body at a desired location without attaching the free ends.

2. The surgical retractor of claim 1, wherein the first radiolucent tip includes a first plurality of tines extending from a distal portion of the first radiolucent tip, wherein the second radiolucent tip includes a second plurality of tines extending from a distal portion of the second radiolucent tip, wherein the second plurality of tines are adjacent to the first plurality of tines when the surgical retractor is in a first position, and wherein the first and second pluralities of tines are spaced apart from one another to engage a surgical incision when the surgical retractor is in a second position.

3. The surgical retractor of claim 2, wherein a portion of the body disposed proximate of the holder includes a ratchet pawl assembly configured to prevent movement of the surgical retractor towards the first position once the surgical retractor has been forced into the second position.

4. The surgical retractor of claim 1, wherein the holder is rotatably coupled to the body such that the holder is free to rotate about the body axis.

5. The surgical retractor of claim 1, wherein the first and second radiolucent tips are formed of aluminum.

6. The surgical retractor of claim 1, wherein the body is formed of stainless steel.

7. The surgical retractor of claim 1, wherein the distal portion of the first portion of the body includes a first hole and the distal portion of the second portion of the body includes a second hole, wherein the first radiolucent tip includes a third hole and the second radiolucent tip includes a fourth hole, and wherein the surgical retractor further comprises:
   a first pin extending through the first and third holes to couple the first radiolucent tip to the first portion of the body; and
   a second pin extending through the second and fourth holes to couple the second radiolucent tip to the second portion of the body.

8. A handheld surgical retractor; comprising:
   a body extending from a proximal end to a distal end and having a first portion coupled to a second portion via a hinged connection, wherein the first and second portions are configured to rotate about a body axis, and wherein a distal portion the first portion of the body includes a first hole and a distal portion of the second portion of the body includes a second hole;
   a first radiolucent tip coupled to the distal portion of the first portion and having a third hole corresponding to the first hole;
   a second radiolucent tip coupled to the distal portion of the second portion and having a fourth hole corresponding to the second hole;
   a first pin extending through the first and third holes to couple the first radiolucent tip to the first portion of the body;
   a second pin extending through the second and fourth holes to couple the second radiolucent tip to the second portion of the body;
   a holder coupled to one of the first or second portions; and
   a deformable member extending through the holder and having a first free end and a second free end opposite the first free end, wherein the deformable member is configured to be deformed around human tissue to facilitate fixation of the body of the handheld surgical retractor at a desired location without attaching the free ends.

9. The handheld surgical retractor of claim 8, wherein the first radiolucent tip includes a first plurality of tines extending from a distal portion of the first radiolucent tip, wherein the second radiolucent tip includes a second plurality of tines extending from a distal portion of the second radiolucent tip, wherein the second plurality of tines are adjacent to the first plurality of tines when the handheld surgical retractor is in a first position, and wherein the first and second pluralities of tines are spaced apart from one another to engage a surgical incision when the handheld surgical retractor is in a second position.

10. The handheld surgical retractor of claim 9, wherein a portion of the body disposed proximate of the holder includes a ratchet pawl assembly configured to prevent movement of the handheld surgical retractor towards the first position once the handheld surgical retractor has been forced into the second position.

11. The handheld surgical retractor of claim 8, wherein the holder is rotatably coupled to the body such that the holder is free to rotate about the body axis.

12. The handheld surgical retractor of claim 8, wherein the first and second radiolucent tips are formed of aluminum.

13. The handheld surgical retractor of claim 8, wherein the body is formed of stainless steel.

14. A surgical retractor; comprising:
   a body extending from a proximal end to a distal end and having a first portion coupled to a second portion via a hinged connection, wherein the first and second portions are configured to rotate about a body axis;
   a first radiolucent tip coupled to a distal portion of the first portion; and
   a second radiolucent tip coupled to a distal portion of the second portion;
   a deformable shaft coupled to the body member and having a first free end and a second free end, the deformable shaft adapted to deform around human tissue to facilitate fixation of the body of the surgical retractor at a desired location without attaching the free ends.

15. The surgical retractor of claim 14, wherein the first radiolucent tip includes a first plurality of tines extending from a distal portion of the first radiolucent tip, wherein the second radiolucent tip includes a second plurality of tines extending from a distal portion of the second radiolucent tip, wherein the second plurality of tines are adjacent to the first plurality of tines when the surgical retractor is in a first position, and wherein the first and second pluralities of tines are spaced apart from one another to engage a surgical incision when the surgical retractor is in a second position.

16. The surgical retractor of claim 14, further comprising:
   a holder coupled to the body, the deformable shaft being attached to the holder and extending through the holder.

17. The surgical retractor of claim 16, wherein a portion of the body disposed proximate of the holder includes a ratchet pawl assembly configured to prevent movement of the surgical retractor towards a first position once the surgical retractor has been forced into a second position.

18. The surgical retractor of claim 16, wherein the holder is rotatably coupled to the body such that the holder is free to rotate about the body axis.

19. The surgical retractor of claim 14, wherein the distal portion of the first portion of the body includes a first hole and the distal portion of the second portion of the body includes a second hole, wherein the first radiolucent tip includes a third hole and the second radiolucent tip includes a fourth hole, and wherein the surgical retractor further comprises:
   a first pin extending through the first and third holes to couple the first radiolucent tip to the first portion of the body; and
   a second pin extending through the second and fourth holes to couple the second radiolucent tip to the second portion of the body.

20. The surgical retractor of claim 14, wherein the first and second radiolucent tips are formed of aluminum.

\* \* \* \* \*